United States Patent
Hong et al.

(10) Patent No.: US 12,246,108 B2
(45) Date of Patent: Mar. 11, 2025

(54) MUSSEL INSPIRED NANOCOMPOSITE ADHESIVES FOR BIOMEDICAL APPLICATIONS

(71) Applicant: BOARD OF REGENTS, THE UNIVERSITY OF TEXAS SYSTEM, Austin, TX (US)

(72) Inventors: Yi Hong, Arlington, TX (US); Kytai Nguyen, Arlington, TX (US); Philippe Zimmern, Arlington, TX (US); Jun Liao, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 269 days.

(21) Appl. No.: 17/069,239

(22) Filed: Oct. 13, 2020

(65) Prior Publication Data
US 2021/0106718 A1 Apr. 15, 2021

Related U.S. Application Data

(60) Provisional application No. 62/914,665, filed on Oct. 14, 2019.

(51) Int. Cl.
| | | |
|---|---|---|
| *A61L 24/04* | (2006.01) | |
| *A61L 24/00* | (2006.01) | |
| *C08G 18/18* | (2006.01) | |
| *C08G 18/22* | (2006.01) | |
| *C08G 18/24* | (2006.01) | |
| *C08G 18/30* | (2006.01) | |
| *C08G 18/32* | (2006.01) | |
| *C08G 18/77* | (2006.01) | |

(52) U.S. Cl.
CPC ......... *A61L 24/046* (2013.01); *A61L 24/0015* (2013.01); *A61L 24/0042* (2013.01); *C08G 18/1808* (2013.01); *C08G 18/1833* (2013.01); *C08G 18/227* (2013.01); *C08G 18/246* (2013.01); *C08G 18/307* (2013.01); *C08G 18/3206* (2013.01); *C08G 18/771* (2013.01)

(58) Field of Classification Search
CPC .............. A61L 24/046; A61L 24/0015; A61L 24/0042; C08G 18/1808; C08G 18/771; C08G 18/227; C08G 18/246; C08G 18/307; C08G 18/3206; C08G 18/1833
See application file for complete search history.

(56) References Cited

U.S. PATENT DOCUMENTS 6,497,729 B1 * 12/2002 Moussy ................. A61L 27/54
623/23.57

FOREIGN PATENT DOCUMENTS

| EP | 3103485 | * 12/2016 |
| KR | 20160098343 | * 8/2016 |
| WO | WO 2005063965 | * 12/2004 |
| WO | WO 2017101026 | * 12/2015 |

OTHER PUBLICATIONS

Pandey et al. (Adv Healthc Mater. (2018)7(7):11701069.*
Kim et al. Biomacromolecules (2014), 15, 1579-1585.*

* cited by examiner

*Primary Examiner* — Shirley V Gembeh
(74) *Attorney, Agent, or Firm* — Maynard Nexsen PC; John P. Zimmer; Candice S. Cashman

(57) ABSTRACT

A tissue adhesive composition comprises a biodegradable adhesive; nanoparticles; and a tissue regenerative agent. Methods of adhering tissue comprise applying a film of the tissue adhesive composition to a first surface of a first biological tissue; contacting a second surface of a second biological tissue with the first surface of the first biological tissue, wherein the film of the composition is positioned between and in contact with both the first surface and the second surface.

17 Claims, 18 Drawing Sheets

PLGA     PLGA-NHS     Silica
nanoparticles   nanoparticles   nanoparticles

| Nanoparticle | Size (nm) | Polydispersity |
|---|---|---|
| Silica | 30 ± 13 | 0.19 ± 0.06 |
| PLGA | 212 ± 45 | 0.22 ± 0.07 |
| PLGA-NHS | 237 ± 106 | 0.49 ± 0.15 |

MUSSEL INSPIRED NANOCOMPOSITE ADHESIVES FOR BIOMEDICAL APPLICATIONS

RELATED APPLICATION DATA

The present application claims priority pursuant to 35 U.S.C. § 119(e) to U.S. Provisional Patent Application Ser. No. 62/914,665 filed Oct. 14, 2019 which is incorporated herein by reference in its entirety.

STATEMENT REGARDING GOVERNMENT FUNDING

This invention was made with government support under grant R01 HD097330 awarded by the National Institute of Health. The government has certain rights in the invention.

BACKGROUND

Pelvic organ prolapse (POP) is a condition in which the pelvic organs are displaced, and protrude by varying degrees into the vaginal canal. Affected organs can include the urethra, bladder, rectum, small bowel, uterus, or more commonly, a combination of these pelvic organs. Approximately, 300,000 prolapse surgeries are performed annually in the United States to treat symptomatic POP, with an estimated cost of over $1 billion. Several clinical patient series have estimated that approximately 30-40% of women develop POP, with a lifetime estimate of surgical risk reaching 11-12% by 80 years of age. The predicted increase in the number of women with pelvic floor disorders will increase from 31 to about 42 million between 2015 and 2045. Because recurrence is common after corrective surgery using native tissue repair, with rates approaching 30%, new techniques using a variety of reinforcing synthetic meshes have emerged, such as the use of transvaginal meshes. However, an FDA warning in 2008 has reminded patients and physicians alike in cautiously employing these transvaginal meshes until adequate safety and efficacy records are established in randomized trials. A FDA update in early 2016 issued two orders, one to reclassify these meshes from class II to class III (high-risk devices) and another to require manufacturers to submit a pre-market approval in order to test safety and effectiveness of any new transvaginal mesh for POP. Various Da Vinci robotic or laparoscopic procedures have also been developed, but are more invasive than vaginal surgery, and the risks of infection and extrusion of the synthetic material remain, albeit at different rates.

Consequently, there is an unmet need for methods, devices, and/or compositions to treat POP that alleviates some or all of the issues presented by conventional treatments of POP.

SUMMARY

In one aspect, a tissue adhesive composition comprises a biodegradable adhesive; nanoparticles; and a tissue regenerative agent. In some embodiments, the biodegradable adhesive comprises a functionalized biopolymer. In some embodiments, the biodegradable adhesive comprises a dopamine grafted biopolymer comprising an alginate, polytripeptide (Gly-Tyr-Lys), Mussel Adhesive Protein (MAP), polyethylene glycol (PEG-DOPA), hyaluronic acid (HA) on Pluronic hydrogel, catechol-Ala-Ala-PEG (cAAPEG), poly ((Lys·HBr)$_x$-(DOPA)$_y$), deacetylated chitosan, oxidized and DOPA-functionalized dextran, PEG-dopamine-polycaprolactone (PCL), injectable citrate-based mussel-inspired bioadhesives iCMBAs, anti-bacterial and anti-fungal iCMBAs (AbAf iCs), click iCs, ethylene glycol acrylate methacrylate dopamine (EGAMA-DOPA), poly(dopamine-co-acrylate) (PDA), rfp-1 (MAP), light-activated, mussel protein-based bioadhesive (LAMBA), PEU (poly (CATyr-co-Leu)), PEU (poly (CA-Ser-co-Leu-co-PPG)), POEC-d (octanediol, PEO, citric acid, dopamine), DCTA (gelatin macromer, Fe$^{3+}$, genipin), a polyester, 4-arm-PEG-DA, 4-arm-PEG-PBA, polypeptide-pluronic-polypeptide, or any combination thereof.

In some cases, the biodegradable adhesive comprises a dopamine-grafted alginate. The dopamine-grafted alginate can be crosslinked to form a hydrogel. The biodegradable adhesive is present in a concentration of 1 to 40 wt. %.

In some embodiments, nanoparticles described herein comprise poly(lactic acid) (PLA), poly(glycolic acid) (PGA), poly(lactide-co-glycolide) ("PLGA"), poly(lactide-co-glycolide) N-hydroxysuccinimide ("PLGA-NHS"), poly (lactide-co-glycolide) polydopamine ("PLGA-Dopa") polydopamine, hyaluronic acid-dopamine, silica, poly-(ethylene glycol) (PEG), poly(acryl amide) (PAA), poly (vinyl pyrrolidone) (PVP), poly(caprolactone) (PCL), chitosan, poly-alkyl-cyano-acrylates (PAC), gelatin or any combination thereof. In some instances, the nanoparticles comprise PLGA and/or PLGA-NHS having a weight average molecular weight of 50,000-120,000. In some cases, the nanoparticles have an average particle size in any dimension of 50 nm to 500 nm. In some embodiments, the nanoparticles have an average particle size in any dimension of 250 nm or less. The nanoparticles can be present in a concentration of up to 15 wt. %. In some cases, the nanoparticles are biodegradable.

In some instances, compositions described herein have a lap shear strength of a least 20 kPA when adhered to a biological tissue to tissue interface.

In some embodiments, the tissue regenerative agent comprises a cell recruitment agent, a tissue growth factor, a protein, a microRNA, an exosome, or any combination thereof. The cell recruitment agent can in some cases be a stem cell recruitment agent. In some instances, the cell recruitment agent is stromal cell derived factor-1 alpha ("SDF-1α"). The cell recruitment agent can recruit mesenchymal stromal/stem cells ("MSCs"), hematopoietic stem cell ("HSC"), and/or endothelial progenitor cell ("EPC"). In some embodiments, the cell recruitment agent can increase regenerative cell populations within a biological environment where the composition is present. The cell recruitment agent can be released from the composition into the biological environment over 1-50 days. In some instances, the biological environment is mammalian tissue. An exemplary first biological tissue is vagina wall tissue, and the second biological tissue is detached pelvic muscle.

The cell recruitment agent can be encapsulated in the nanoparticles in some instances, or in other instances, can be present in the biodegradable adhesive.

In another aspect, a method of adhering tissue comprises applying a film of a composition described herein to a first surface of a first biological tissue; contacting a second surface of a second biological tissue with the first surface of the first biological tissue, wherein the film of the composition is positioned between and in contact with both the first surface and the second surface. In one embodiment, the first biological tissue is vagina wall tissue, and the second biological tissue is detached pelvic muscle.

In some embodiments, the method further comprises releasing the tissue regenerative agent into an area proximate to the film of the composition. In some cases, the cell recruitment agent is released for up to 5 weeks. The tissue regenerative agent can be a cell recruitment agent in some cases, and release of the cell recruitment agent can recruit localization of mesenchymal stromal/stem cells ("MSCs"), hematopoietic stem cell ("HSC"), and/or endothelial progenitor cell ("EPC") proximate to the film of the composition. In some embodiments, localization of the cells proximate to the film promotes new tissue formation, tissue repair, and/or tissue regeneration between the first biological tissue and the second biological tissue. In some instances, localization of the cells proximate to the film promotes angiogenesis.

DETAILED DESCRIPTION

All ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

Proactive prevention of complete pelvic muscle detachment from the vaginal wall is a desirable pelvic organ prolapse (POP) treatment, rather than waiting until the process that leads to advanced POP stage and then provide the treatment. Such early detachment can be observed by ultrasound and pelvic MRI studies. Detachment between the pelvic muscle and vaginal wall could be repaired early using a bioadhesive material to restore the support of the vaginal wall in each lateral vaginal sulcus to the adjacent pelvic floor musculature.

Figure 1:
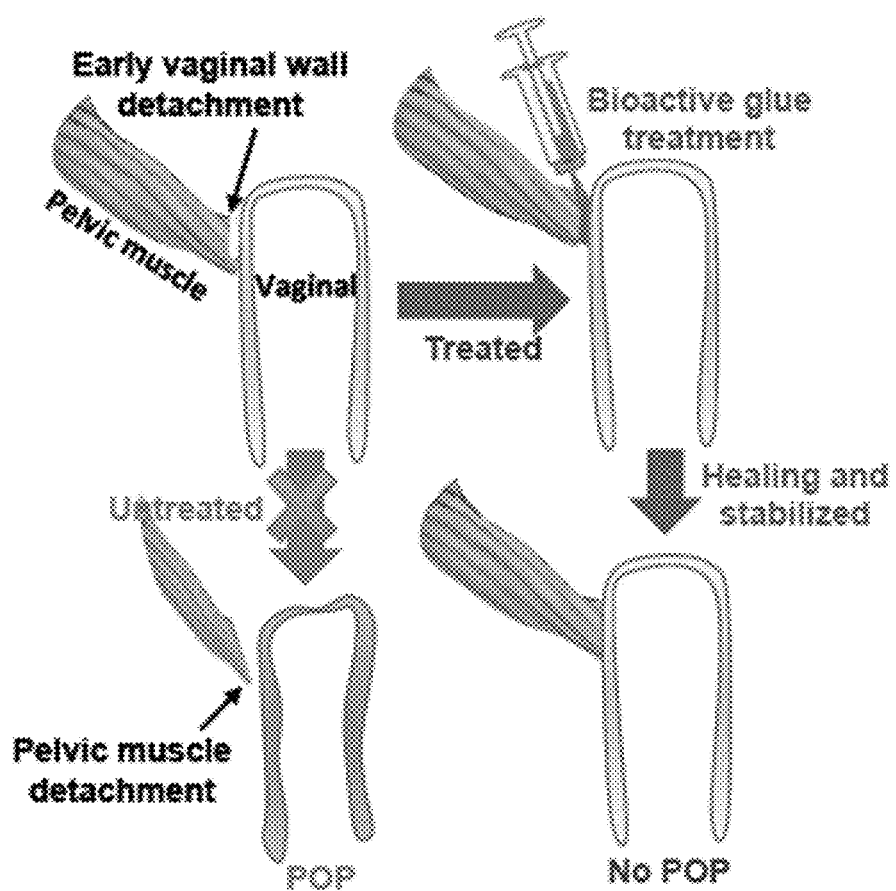
FIG. 1 is a schematic of proactive treatment verses non-treatment of early vaginal wall detachment of pelvic muscle verses.

In addition to mechanically securing the pelvic floor musculature to the vaginal wall, a bioadhesive material that also allows or promotes cell ingrowth and new tissue formation would be especially advantageous for long term success of the treatment. The bioadhesive material would provide an effective support to enhance the vaginal wall attachment while new tissue is being formed. In some embodiments described herein, a bioactive adhesive is used to repair the early detachment between the levator muscle (pelvic muscle) and the vaginal wall, in order to prevent the development of a more advanced anterior vaginal wall prolapse and pelvic organ prolapse. Moreover, bioactive adhesives described herein further comprise a tissue regenerative agent in some embodiments, which promotes cell ingrowth and new tissue formation, and which can in some instances result in biological reattachment of the pelvic muscle to the vaginal wall through the growth of new tissue. As shown for example in FIG. 1, when early anterior vaginal wall detachment of the levator muscle (pelvic muscle) occurs, without treatment, the pelvic muscle and vaginal wall will eventually fully detach, followed by occurrence of POP. However, in instances where bioactive adhesives described herein are used to reattach the vaginal wall to the pelvic muscle, the connection will heal or stabilize the early detachment and prevent further development of POP.

While the use of bioactive adhesives are described herein for the treatment and repair of POP, it is to be understood that POP is merely an exemplary biological condition, and should not be treated as being limiting to the invention unless expressly stated as such. Bioactive adhesives described herein can be used to treat and repair any biological condition, disease, or injury not inconsistent with the objectives of this disclosure, such as hernia repairs, torn ligaments or tendons, torn muscle, broken bones, wound closures or incisions, and the like.

Adhesives derived from synthetic and natural polymers have been used for various tissue adhesions, such as skin and eyes. Predominately cyanoacrylated and poly(ethylene glycol) based synthetic adhesives have been used, which display very strong adhesive properties. However, while strong, these synthetic adhesive polymers are nearly all not degradable and can produce toxic side products, which presents a number of undesirable problems with their use. Fibrin glue is a common biodegradable and biocompatible natural bioadhesive currently available. However, fibrin glue does not form very strong bonds, especially in a wet, in vivo environments. Additionally, reaching the maximum adhesive strength of fibrin glue takes extended amounts of time, which reduces its effectiveness of vaginal wall attachment or other biological tissue attachments. Bioactive adhesives described herein rapidly display maximum adhesive strength in dry, as well as wet, in vivo environments.

Figure 2:
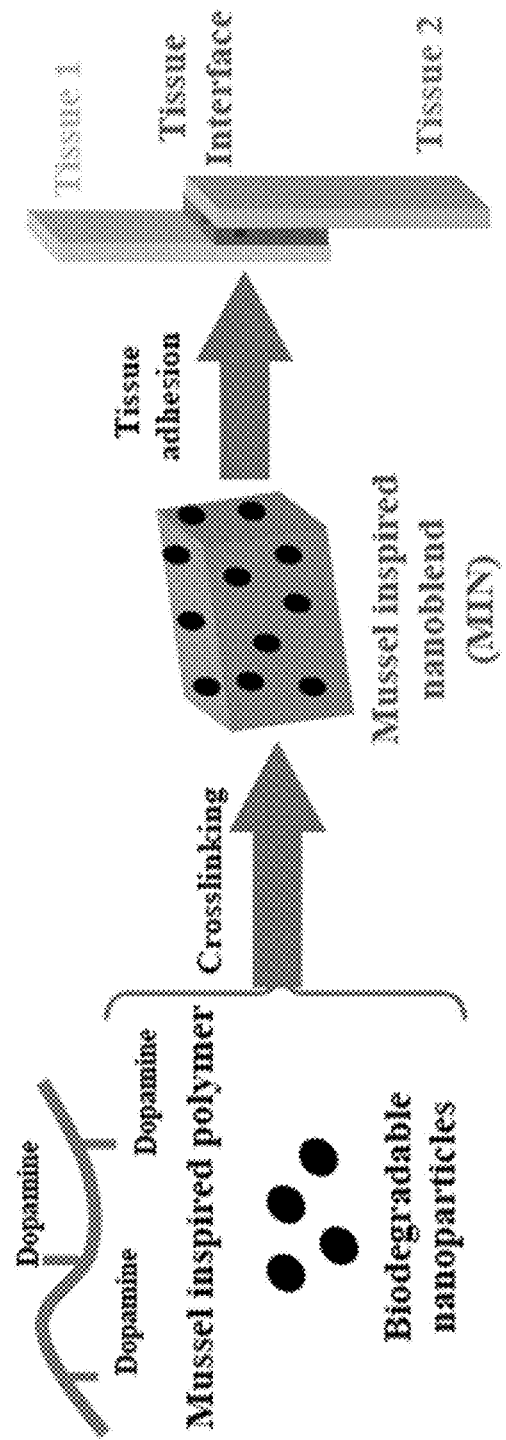
FIG. 2 is a schematic of using a tissue adhesive composition having a biodegradable adhesive and nanoparticles to join two tissue together.

In some embodiments, bioactive adhesives described herein blend a biodegradable nanoparticle (NPs) and mussel-inspired adhesive, which together provide high adhesive strength in the short term, yet will yield full degradation. These bioactive adhesives are usable in early vagina wall detachment of pelvic muscles, and offer sufficient adhesive strength to repair the pelvic floor tear, while being injectable and ultimately biodegradable. Specifically, in FIG. 2, natural polymers are conjugated with dopamine groups and blended with biodegradable nanoparticles, and the blend adhesive, called a mussel inspired nanoblend (MIN), can be cross-linked and then used for tissue gluing.

In addition to the adhesive properties used to glue early detached vaginal wall, bioactive adhesives described herein can in some embodiments load a cell recruiting chemokine SDF-1α into the biodegradable NPs. The long-term release of the SDF-1α from NPs can recruit endogenous stem cells and promote new tissue formation at the detached site to strengthen vaginal wall attachment. In some embodiments, bioactive adhesives described herein can rapidly cure in wet environments, such as within a biological cavity. For example, bioactive adhesives can cure at an interface between vaginal wall and pelvic floor musculature. In some cases, this wet curing ability of the bioactive adhesive reduces morbidity and cost associated with more complex repairs for advanced POP or other biological repairs that often generate higher surgical risks.

I. Tissue Adhesive Compositions

In an aspect, a tissue adhesive composition comprises a biodegradable adhesive; nanoparticles; and a tissue regenerative agent. In some cases, the biodegradable adhesive is a natural bio-polymer, although in other cases, the biodegradable adhesive is a synthetic polymer.

The biodegradable adhesive comprises a functionalized biopolymer, where in some embodiments, the functionalized biopolymer is a catechol or dopamine-grafted biopolymer. In a preferred embodiment, the functionalized biopolymer is a dopamine-grafted biopolymer.

The biodegradable adhesive can be any biodegradable polymer not inconsistent with the objective of this disclosure. In some embodiments, the biodegradable adhesive comprises a dopamine grafted alginate, polytripeptide (Gly-Tyr-Lys), Mussel Adhesive Protein (MAP), polyethylene glycol (PEG-DOPA), hyaluronic acid (HA) on Pluronic hydrogel, catechol-Ala-Ala-PEG (cAAPEG), poly((Lys·HBr)$_x$-(DOPA)$_y$), deacetylated chitosan, oxidized and DOPA-functionalized dextran, PEG-dopamine-polycaprolactone (PCL), injectable citrate-based mussel-inspired bioadhesives iCMBAs, anti-bacterial and anti-fungal iCMBAs (AbAf iCs), click iCs, ethylene glycol acrylate methacrylate dopamine (EGAMA-DOPA), poly(dopamine-co-acrylate) (PDA), rfp-1 (MAP), light-activated, mussel protein-based bioadhesive (LAMBA), PEU (poly (CATyr-co-Leu)), PEU (poly (CA-Ser-co-Leu-co-PPG)), POEC-d (octanediol, PEO, citric acid, dopamine), DCTA (gelatin macromer, $Fe^{3+}$, genipin), a polyester, 4-arm-PEG-DA, 4-arm-PEG-PBA, polypeptide-pluronic-polypeptide, or any combination thereof.

The biodegradable polymer can have a weight average molecular weight of 20,000-200,000, 25,000-175,000, 30,000-165,000, 35,000-155,000, 40,000-135,000, 45,000-125,000, 50,000-120,000, 60,000-110,000, 70,000-100,000, 80,000-90,000, 40,000-200,000, 60,000-200,000, 80,000-200,000, 100,000-200,000, 120,000-200,000, 140,000-200,000, 160,000-200,000, 20,000-180,000, 20,000-160,000, 20,000-140,000, 20,000-120,000, 20,000-100,000, 20,000-80,000, 20,000-60,000, or 20,000-40,000.

In some embodiments, the biodegradable adhesive comprises a dopamine-grafted alginate. The dopamine-grafted alginate can be crosslinked to form a hydrogel using any cross-linking agent not inconsistent with the objectives of this disclosure. In some instances, the cross-linking agent comprises sodium periodate, $FeCl_3$, $CaCl_2$, $MgCl_2$, or any other known alginate cross-linking agent.

When the biodegradable adhesive comprises biodegradable polymers other than dopamine-grafted alginate, any cross-linking agent not inconsistent with the objectives of this disclosure can be used.

The biodegradable adhesive can present in a concentration of 1 to 40 wt. %, 1-38 wt. %, 1-36 wt. %, 1-34 wt. %, 1-32 wt. %, 1-30 wt. %, 1-28 wt. %, 1-26 wt. %, 1-24 wt. %, 1-22 wt. %, 1-20 wt. %, 1-18 wt. %, 1-16 wt. %, 1-14 wt. %, 1-12 wt. %, 1-10 wt. %, 1-8 wt. %, 1-5 wt. %, 3-40 wt. %, 6-40 wt. %, 8-40 wt. %, 10-40 wt. %, 12-40 wt. %, 14-40 wt. %, 16-40 wt. %, 18-40 wt. %, 20-40 wt. %, 22-40 wt. %, 24-40 wt. %, 26-40 wt. %, 28-40 wt. %, 30-40 wt. %, 32-40 wt. %, 5-35 wt. %, 10-30 wt. %, 15-25 wt. %, 5 wt. %, 10 wt. %, 15 wt. %, 20 wt. %, 25 wt. %, 30 wt. %, 35 wt. %, or 40 wt. %.

Nanoparticles described herein can be a biodegradable nanoparticle that is natural, synthetic, or both in origin. In some embodiments, the nanoparticles comprise poly(lactic acid) (PLA), poly(glycolic acid) (PGA), poly(lactide-co-glycolide) ("PLGA"), poly(lactide-co-glycolide) N-hydroxysuccinimide ("PLGA-NHS"), poly(lactide-co-glycolide) polydopamine ("PLGA-Dopa")polydopamine, hyaluronic acid-dopamine, silica, poly-(ethylene glycol) (PEG), poly (acryl amide) (PAA), poly(vinyl pyrrolidone) (PVP), poly (caprolactone) (PCL), chitosan, poly-alkyl-cyano-acrylates (PAC), gelatin, or any combination thereof.

In some embodiments, the biodegradable nanoparticles comprise PLGA and/or PLGA-NHS. The PLGA and/or PLGA-NHS nanoparticles can have a weight average molecular weight of 20,000-200,000, 25,000-175,000, 30,000-165,000, 35,000-155,000, 40,000-135,000, 45,000-125,000, 50,000-120,000, 60,000-110,000, 70,000-100,000, 80,000-90,000, 40,000-200,000, 60,000-200,000, 80,000-200,000, 100,000-200,000, 120,000-200,000, 140,000-200,000, 160,000-200,000, 20,000-180,000, 20,000-160,000, 20,000-140,000, 20,000-120,000, 20,000-100,000, 20,000-80,000, 20,000-60,000, or 20,000-40,000.

The biodegradable nanoparticles can have an average particle size in any dimension of 10 nm to 1000 nm, 10 nm to 900 nm, 10 nm to 800 nm, 10 nm to 700 nm, 10 nm to 600 nm, 10 nm to 500 nm, 10 nm to 400 nm, 10 nm to 300 nm, 10 nm to 200 nm, 10 nm to 100 nm, 30 nm to 1000 nm, 50 nm to 1000 nm, 75 nm to 1000 nm, 100 nm to 1000 nm, 200 nm to 1000 nm, 300 nm to 1000 nm, 400 nm to 1000 nm, 500 nm to 1000 nm, 600 nm to 1000 nm, 50 nm to 500 nm, 65 nm to 450 nm, 85 nm to 400 nm, 100 nm to 375 nm, 125 nm to 350 nm, 150 nm to 325 nm, 175 nm to 300 nm, 200 nm to 275 nm, 225 nm to 250 nm, 400 nm or less, 375 nm or less, 350 nm or less, 325 nm or less, 300 nm or less, 275 nm or less, 250 nm or less, 225 nm or less, 200 nm or less, 175 nm or less, 150 nm or less, 125 nm or less, or 100 nm or less.

Nanoparticles can be present in the composition in any concentration not inconsistent with the objectives of this disclosure. In some embodiments, nanoparticles are present in a concentration of up to 1 wt. %, up to 5 wt. %, up to 7 wt. %, up to 9 wt. %, up to 10 wt. %, up to 11 wt. %, up to 12 wt. %, up to 13 wt. %, up to 14 wt. %, up to 15 wt. %, up to 16 wt. %, up to 17 wt. %, up to 18 wt. %, up to 19 wt. %, up to 20 wt. %, 1-20 wt. %, 3-17 wt. %, 5-15 wt. %, 7-13 wt. %, 9-11 wt. %, or 1-15 wt. %.

In some embodiments, the nanoparticles are blended with the biodegradable adhesive. Inclusion of nanoparticles in the biodegradable adhesive can increase the adhesive strength of the tissue adhesive composition to levels greater than an adhesive strength of the nanoparticles or the biodegradable adhesive alone.

Tissue adhesive compositions described herein can have a lap shear strength of at least 10 kPA, 13 kPA, 15 kPA, 17 kPA, 20 kPA, 22 kPA, 25 kPA, 27 kPA, 30 kPA, 32 kPA, 35 kPA, or greater than 35 kPA when adhered to a biological tissue to tissue interface.

Tissue adhesive compositions described herein can be present in mammalian tissue for 2 weeks, 3 weeks, 4 weeks, 5 weeks, 6 weeks, 7 weeks, 8 weeks, 9 weeks, 10 weeks, 11 weeks, 12 weeks, or greater than 12 weeks before biodegrading.

In some embodiments, tissue adhesive compositions can comprise a tissue regenerative agent. Any type of tissue regenerative agent can be used that is not inconsistent with the objectives of this disclosure. For example, in some cases the tissue regenerative agent comprises a cell recruitment agent, a tissue growth factor, a protein, a cytokine, an siRNA, a noncoding RNA, a microRNA, an exosome, or any combination thereof. Exemplary tissue growth factors can comprise, basic fibroblast growth factor (bFGF), transforming growth factor beta (TGF-beta), vascular endothelial growth factor (VEGF), insulin-like growth factor (IGF), and/or any other tissue growth factor. Exemplary proteins can comprise collagen, gelatin, elastin, or any other protein. Exemplary cytokine, siRNA, noncoding RNA, and microRNA can be any such example that assists, recruits, or directly affects tissue regeneration and genesis. Exemplary exosomes can comprise any muscle cell-derived exosome, such as exosomes derived from MSCs, human-induced pluripotent stem cells (hIPSs), muscle stem cells, endothelial progenitor cells (EPCs), and the like.

In an embodiment, the cell recruitment agent is a stem cell recruitment agent. Endogenous stem cell recruitment can localize the stem cells at the location of the tissue repair site, allowing in some cases differentiation of the stem cells into the same cell types as the tissue being repaired. The cell recruitment agent can be stromal cell derived factor-1 alpha ("SDF-1α") in some cases. SDF-1α is a chemoattractant that can recruit endogenous stem cells to the localized release site in the tissue, such as ischemia heart and skin. The SDF-1α can bind with its CXCR4 receptor on stem and progenitor cells, which regulate bone marrow derived stem cell homing and repopulation and mobilizes stem cells into the peripheral blood. In some embodiments, release of SDF-1α recruits mesenchymal stromal/stem cells (MSCs), hematopoietic stem cell (HSC), endothelial progenitor cell (EPC) and/or other specific stem cells surrounding the damaged tissue, which can significantly increase regenerative cell populations locally and promote new tissue formation. Additionally, long-term chemokine release of SDF-1α can more effectively recruit the stem cells and promote tissue regeneration. In some cases, the recruited stem cells can differentiate into the primary cell population in situ, which can assistant in the tissue repair and regeneration. Accordingly, in some cases, the cell recruitment agent increases regenerative cell populations within a biological environment where the composition is present.

The tissue regenerative agent can be loaded on, absorbed by, or encapsulated in the nanoparticles. When in a biological environment, the tissue regenerative agent can be quickly or slowly released from the tissue adhesive composition into the biological environment over a period of time. In some embodiments, the tissue regenerative agent is released from the composition into the biological environment over 1-50 days, such as 1 day, 5 days, 8 days, 10 days, 13 days, 15 days, 18 days, 20 days, 23 days, 26 days, 30 days, 33 days, 36 days, 40 days, 43 days, 46 days, 50 days, 53 days, 56 days, 60 days, or greater than 60 days.

II. Methods of Using Adhesive Compositions

In another aspect, a method of adhering tissue comprises applying a film of a composition described in Section I herein to a first surface of a first biological tissue; and contacting a second surface of a second biological tissue with the first surface of the first biological tissue, wherein the film of the composition is positioned between and in contact with both the first surface and the second surface. The method can further comprise releasing the tissue regenerative agent into an area proximate to the film of the composition.

In some embodiments, release of the tissue regenerative agent causes recruitment and localization of the tissue regenerative cells proximate to the film promotes new tissue formation, tissue repair, and/or tissue regeneration between the first biological tissue and the second biological tissue. In some cases, localization of the tissue regenerative cells proximate to the film promotes angiogenesis.

In some embodiments, the first biological tissue is vaginal wall tissue, and the second biological tissue is detached pelvic muscle. Thus, in cases of POP, torn or detached pelvic muscle can be reattached to the vaginal wall tissue, and the recruitment and localization of the tissue regenerative cells can promote new tissue formation, tissue repair, and/or tissue regeneration.

The embodiments described herein can be understood more readily by reference to the following EXAMPLES. Elements, apparatus and methods described herein, however, are not limited to the specific embodiments presented in the EXAMPLES. It should be recognized that these sections describe embodiments and examples that are merely illustrative of the principles of this disclosure. Numerous modifications and adaptations will be readily apparent to those of skill in the art without departing from the spirit and scope of the disclosure. While POP is described in more detail herein, it is to be understood that POP is merely one biological example, and should not be interpreted as limiting to this disclosure. bioactive adhesives described herein can be used to repair or assist in repairing any biological tissue not contrary to the objectives of this disclosure, including the repair of ligaments, cartilage, bone, muscle, organs, or any other tissue type.

Example 1

Dopamine-Grafted Alginate (Alg-Dopa) Synthesis

Alginate is a nature polymer isolated from seaweeds, and has been widely used for biomedical applications with FDA approval. As the alginate contains hydroxyl and carboxyl groups, can be grafted with different functional groups to achieve new functions and physical properties. For instance, alginate can be oxidized to obtain the aldehyde groups, which can then react with the amine groups (e.g. dopamine and peptide) through the Schiff base reaction. The properties of the modified alginate are dependent to the content and type of grafted functional moieties. Alginate hydrogel properties, including water adsorption, adhesive strength and degradation, are related to the grafted dopamine amount, polymer concentration, crosslinking agent type and the like. Furthermore, the nanoparticle characteristics are dependent on size and surface groups.

Figure 3A:
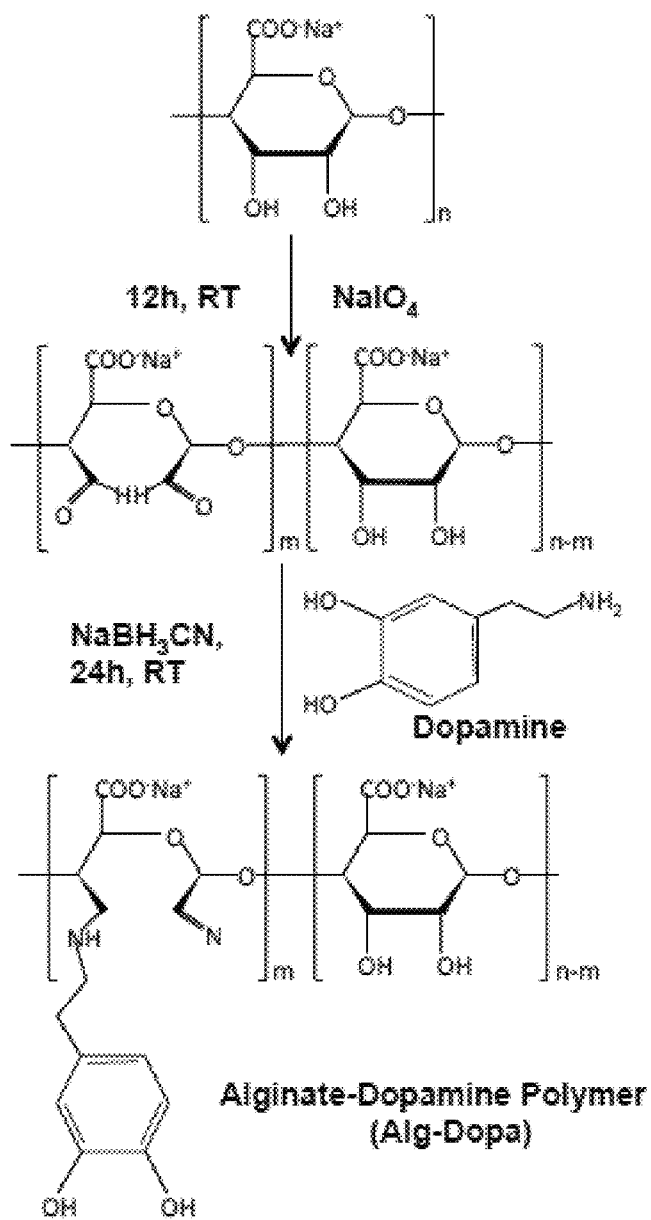
FIG. 3A is a synthetic reaction converting alginate to an alginate dopamine polymer.
Figure 3B:
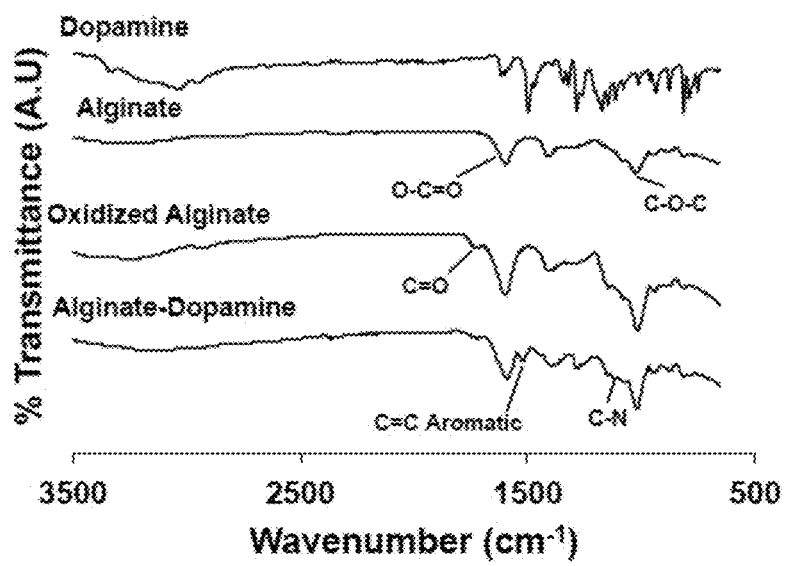
FIG. 3B is an Fourier Transform Infrared spectra of the different synthetic intermediates and product shown in FIG. 3A.

To synthesize the dopamine-grafted alginate (Alg-Dopa), alginate was oxidized to form aldehyde-functionalized alginate (Alg-CHO) according to known methods, and then dopamine molecules were introduced onto Alg-CHO through an Schiff reaction of coupling —CHO and —$NH_2$, as illustrated in the reaction scheme of FIG. 3A. The Alg-CHO can obtained by oxidation using sodium periodate. Specifically, sodium alginate will be reacted with sodium periodate in the dark. The resulted polymer can then subjected to dialysis (MWCO 3.5 kDa) against deionized water and subsequently lyophilized to obtain Alg-CHO. The CHO amounts can be tuned by altering reaction time and the sodium periodate concentration. The CHO content in the Alg-CHO is related to the grafted dopamine content in the next step. The dopamine can be conjugated with Alg-CHO through Schiff reaction in the presence of sodium cyanoborohydride for 24 hours. The obtained solution is purified via dialysis (MWCO 3.5 kDa) against de-ionized water at 4° C. to remove unreacted small molecules and residues, and then lyophilized to obtain the Alg-Dopa. Besides CHO content, the grafted dopamine content is also related to dopamine feed ratio and reaction time. The dopamine content in the polymer is relevant with the adhesive strength of the final adhesive. The chemical structures of Alg-CHO and Alg-Dopa are verified through FTIR and NMR, as shown in the FTIR spectra in FIG. 3B. The dopamine content will be quantified using UV-Visible spectrometry by utilizing the absorption maxima at 280 nm of the aromatic ring in dopamine and determined against standards. A standard curve of dopamine can be achieved by measuring a series of solutions with known dopamine concentration. Molecular weights of alginate (32-400 kDa), alginate/sodium periodate ratio (1/1 to 1/10), and reaction time (12 h-48 h) can be altered to achieve various Alg-Dopas for next steps.

Figure 3C:
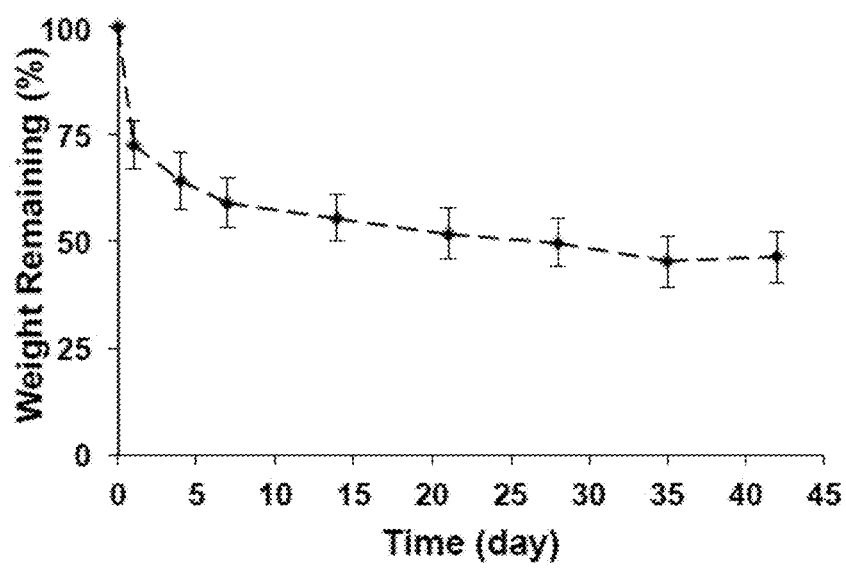
FIG. 3C is a graphic of alginate-dopamine polymer degradation kinetics in PBS at 37° C.

The dopamine-grafting amount was measured using UV-Visible spectrometry, and it was found to be 0.30±0.03 mg/mg Alg-Dopa. As shown in FIG. 3A, Alg-Dopa can be crosslinked using an initiator of sodium periodate. The degradation of the hydrogel was measured in PBS at 37° C., and the mass loss reached 50% after 42 days immersion (FIG. 3C).

To obtain a hydrogel, the obtained Alg-Dopa is dissolved in water or PBS, with the solution forming a solidified hydrogel after adding a crosslinker. The hydrogel properties are tuned by altering polymer concentration (1-40%), and crosslinker type and concentration (1-15%). Different crosslinkers, including sodium periodate and $FeCl_3$, are utilized for the hydrogel formation to select the optimal crosslinkers with good crosslinking and biosafety. The gelation time of the hydrogel is recorded on a rheometer. The water adsorption and swelling ratio are detected in PBS at 37° C. The degradation will be measured in PBS at 37° C. The hydrogel mechanical properties are measured using a rheometer.

Example 2

PLGA and PLGA-NHA Synthesis

Figures 4A, 4B:
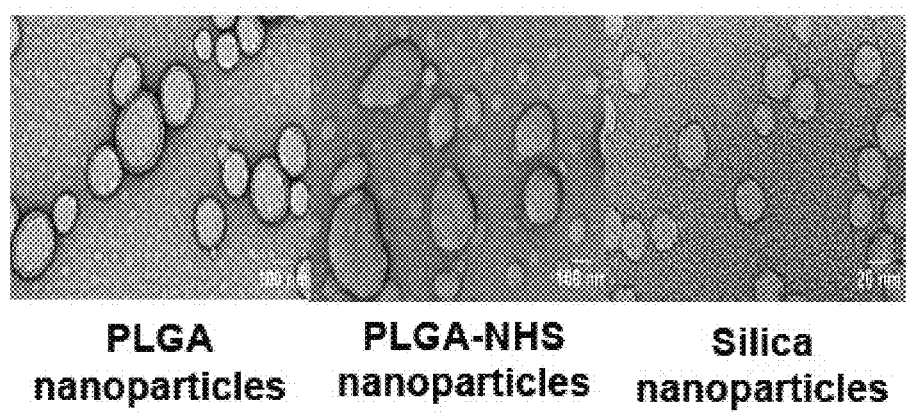
FIG. 4A is a transmission electron microscopy (TEM) image of nanoparticle sizes and morphologies of PLGA, PLGA-NHS and silica nanoparticles.
FIG. 4B is a table listing the nanoparticle sizes and morphologies of PLGA, PLGA-NHS and silica nanoparticles shown in FIG. 4A.
Figure 4C:
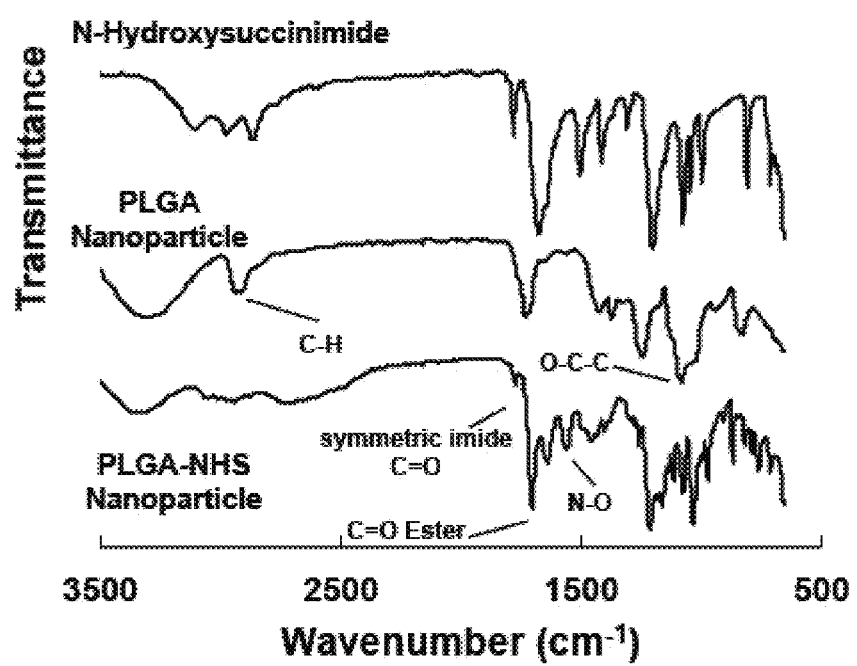
FIG. 4C is an FTIR spectra showing NHS grafting onto PLGA nanoparticle surface to form PLGA-NHS nanoparticles.

Nanoparticles (NPs) were fabricated from biodegradable polymer poly(lactide-co-glycolide) (PLGA) with carboxyl end groups using a conventional emulsion methods (FIG. 4A). The size of NPs is 212±45 nm (FIG. 4B). The nanoparticle was further modified by grafting NHS on the surface through coupling carboxyl and hydroxyl group using 1-ethyl-3-(-3-dimethylaminopropyl) carbodiimide (EDAC) to form PLGA-NHS. After NHS grafting, the NPs size was approximately 237±106 nm, which is slightly increased compared to that of the unfunctionalized PLGA NPs. The NHS grafting can enhance the interaction between NPs and tissues because the succimide can directly react with amine groups of the proteins in the tissue. FTIR further confirmed such chemical reaction (FIG. 4C).

Briefly, biodegradable PLGA (50/50, Mw=65,000-107, 000) with two carboxyl end groups can used for nanoparticle fabrication through single emulsion technique. A PLGA solution in dichloromethane is added dropwise to a polyvinyl alcohol (PVA) solution (5% w/v in deionized water), and sonicated (30 W, 5 min) to form nanoparticles and then stirred overnight at room temperature to allow solvent evaporation. The resulting nanoparticle suspension is centrifuged (15,000 rpm, 30 min), and then lyophilized to obtain PLGA NPs. The nanoparticle size is controlled to be approximately 200 nm by altering polymer concentration and oil/water phase ratio according to known methods, and is verified using dynamic light scattering (DLS). SEM and TEM are used to observe the nanoparticle morphology.

The PLGA NP surface has many carboxyl groups, which allows conjugating functional moieties to enhance the adhesive strength. A PLGA nanoparticle solution in 4-Morpholineethanesulphonic acid (MES) buffer (pH 4.75) is mixed with 1-ethyl-3-(3-dimethylaminopropyl) carbodiimide (EDC) for 30 minutes at room temperature. Then NHS is added to the solution for 2 hours at room temperature, which facilitates the grafting of NHS onto the surface of PLGA nanoparticles. The PLGA-NHS nanoparticles are collected by centrifugation at 15,000 rpm for 30 minutes at 10° C., and then washed with deionized water and lyophilized. The nanoparticle size is measured using DLS, and the resulting morphology is observed by SEM and TEM.

Example 3

Tissue Adhesive Compositions

Figure 5A:
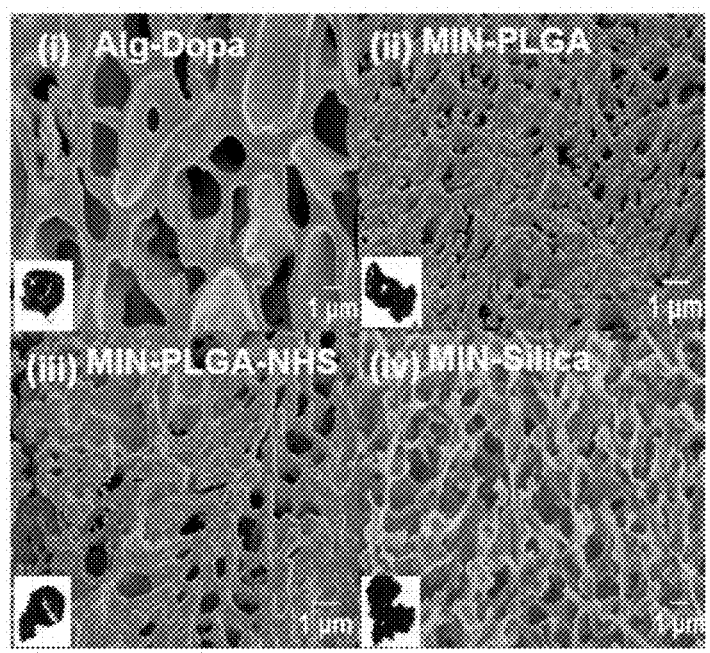
FIG. 5A is a scanning electron microscope (SEM) image showing the morphologies of Alg-Dopa alone and nanoblend adhesives.
Figure 5B:
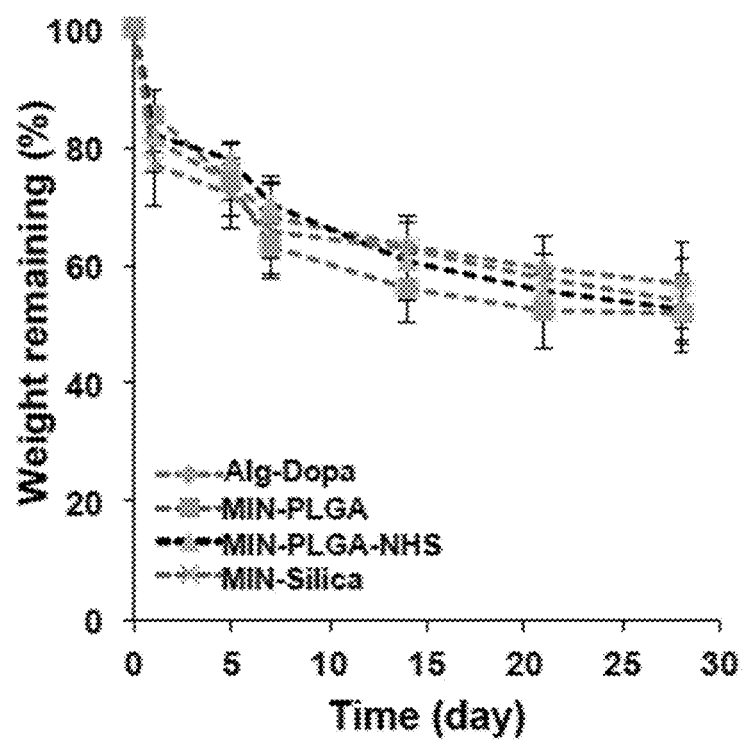
FIG. 5B is a graphical display of the hydrolytic degradation kinetics of Alg-Dopa and various nanoblend adhesives shown in FIG. 5A.

The Alg-Dopa prepared according to EXAMPLE 1 was combined with the different nanoparticles prepared in EXAMPLE 2 as a blend adhesive to form tissue adhesive compositions described herein. In a typical preparation, the Alg-Dopa solution is first blended with the NPs, the crosslinker is then added into the blend, followed by the hydrogel/ nanoparticle blend formation. A series of hydrogel/nanoparticle blends are formed by altering Alg-Dopa concentration, crosslinker concentration and nanoparticle content/size. The morphology of the blend is observed under a SEM after frozen in liquid nitrogen. The gelation time is recorded using a rheometer. The degradation will be measured in PBS at 37° C., and all degradation products will be collected for further toxicity test. As shown in FIG. 5A, Alg-Dopa by itself without any showed a porous structure. However, after blending with different nanoparticles of EXAMPLE 2, the pore size was significantly reduced. The Alg-Dopa and Alg-Dopa blended with nanoparticles (MIN) showed similar degradation kinetics, as shown in FIG. 5B.

Figure 5C:
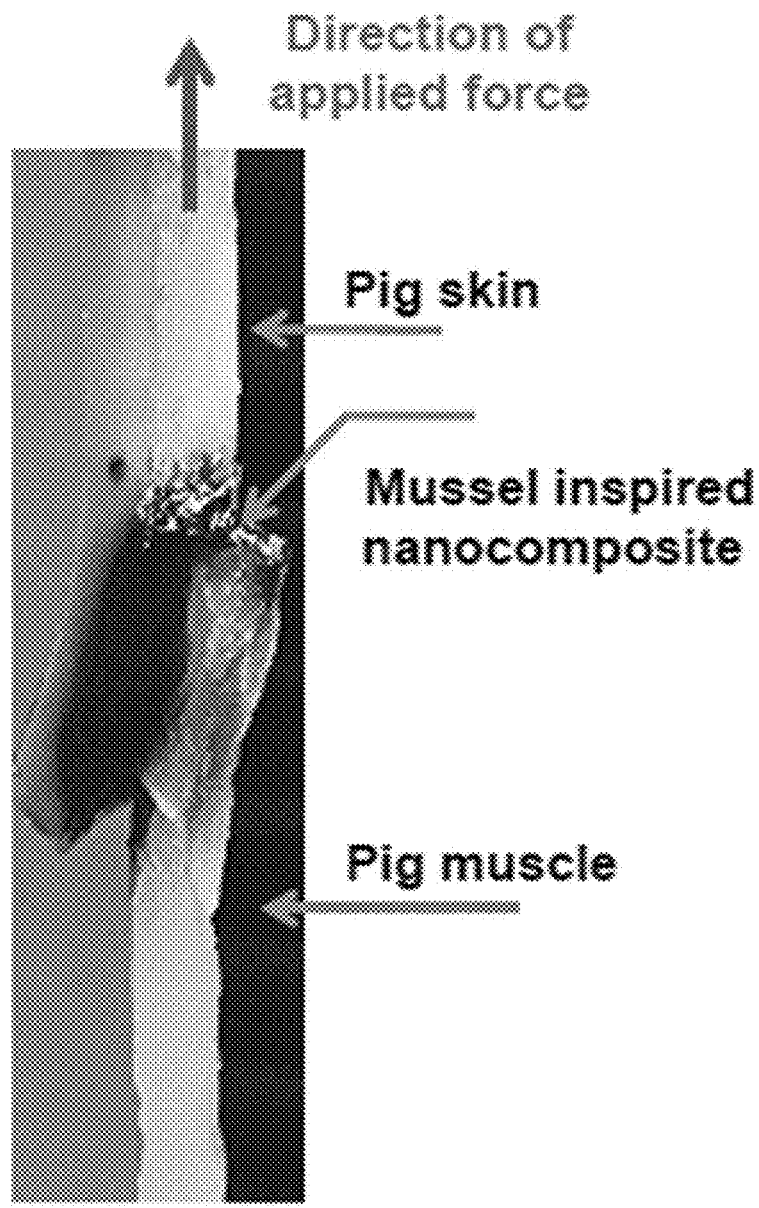
FIG. 5C is a picture of a porcine skin adhered to porcine muscle using an adhesive nanoblend of Alg-Dopa and PLGA.
Figure 5D:
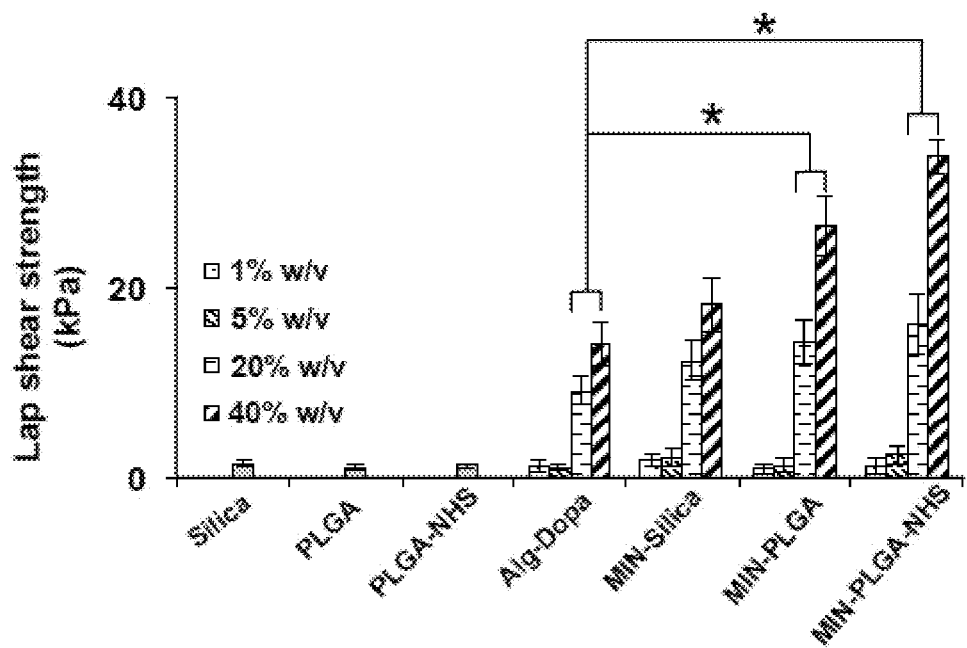
FIG. 5D is a graphical display of the lap shear strength of various adhesives of the porcine skin and porcine muscle shown in FIG. 5C.
Figure 5E:
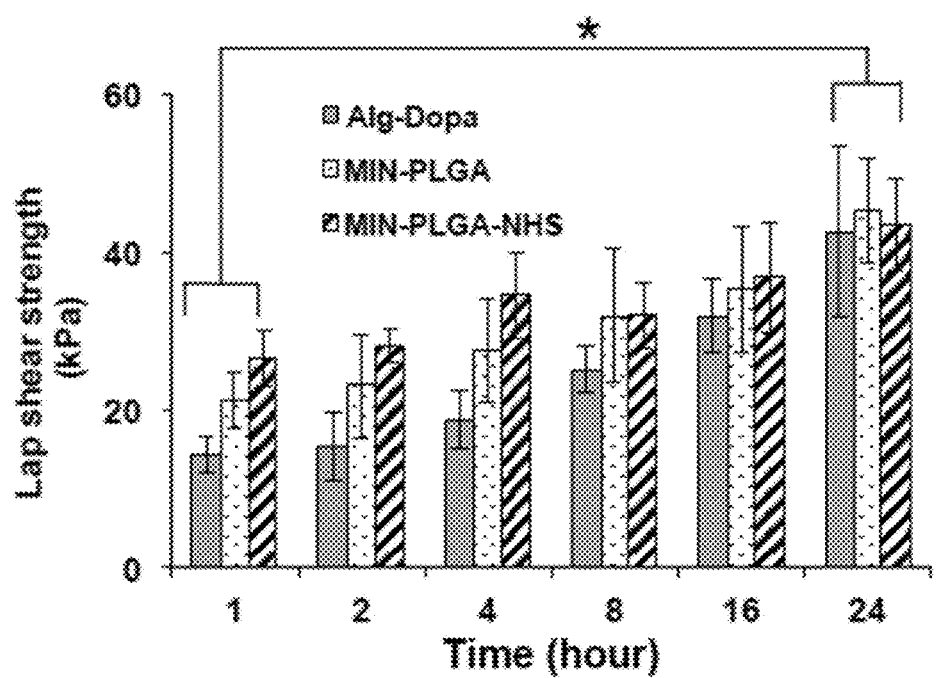
FIG. 5E is a graphical display of the adhesive strength change of the adhesives in FIG. 5D after 24 hours.

The adhesives were pasted on a porcine muscle and skin interface (FIG. 5C) to test adhesive strength and curing time. After 1 hour, tensile mechanical testing was used to measure the adhesive strength. Compared to the two nanoparticles alone and Alg-Dopa hydrogel alone at the same concentration, the nanoblends significantly increase the adhesive strength. As shown in FIG. 5D, the silicon NPs (Si NP), PLGA NPs and PLGA-NHS NPs alone showed lower than 5 kPa lap shear strength. The alginate-Dopa hydrogel exhibited the concentration-dependent lap shear strength. When the Alg-Dopa concentration was 40%, the lap shear strength was ~15 kPa. After the Alg-Dopa hydrogel was blended with silicon NPs (12.5 wt %) and PLGA NPs (12.5 wt %), the lap shear strengths increased. For a blend of PLGA NPs and Alg-Dopa 40% (MIN-PLGA), the strength was 25 kPa. Furthermore, when PLGA-NHS NPs were involved in the blend, a higher adhesive strength (30 kPa) was displayed than for MIN-PLGA. The adhesive lap shear strength change of the adhesives at different times over 24 h was also measured, as shown in FIG. 5E. As shown, strength increased with time, but at an early stage (1-4 h), the nanoparticle involvement in the Alg-Dopa adhesive significantly increased the adhesive strength compared to Alg-Dopa alone.

Example 4

Tissue Adhesive Compositions with SDF-1α

The SDF-1α release can recruit CXCR4+ cells including MSCs, EPCs and HSCs, and promote the angiogenesis and new tissue formation at the implant site. Stem cell recruitment ability of varieties of the nanoparticle/hydrogel blends described in EXAMPLE 3 are investigated in vitro and in vivo and the optimal sample is selected for studying SDF-1α releasing bioactive glue. The SDF-1α release dosage has been observed in other contexts to have an effect on cell recruitment. Samples with SDF-1α contents (low, medium and high) are selected, which can be achieved by fixed nanoparticle amount with various SDF-1α loading content in the nanoparticles. The mechanical properties of the tissue adhesive do not significantly change. The in vitro cell recruitment is assessed through stem cell migration using transwell culture system. In vivo stem cell recruitment and tissue formation, adhesive strength and material safety are evaluated by implantation into a rat abdominal wall incision model with mechanical testing, histological and immunohistological staining.

Figure 6A:
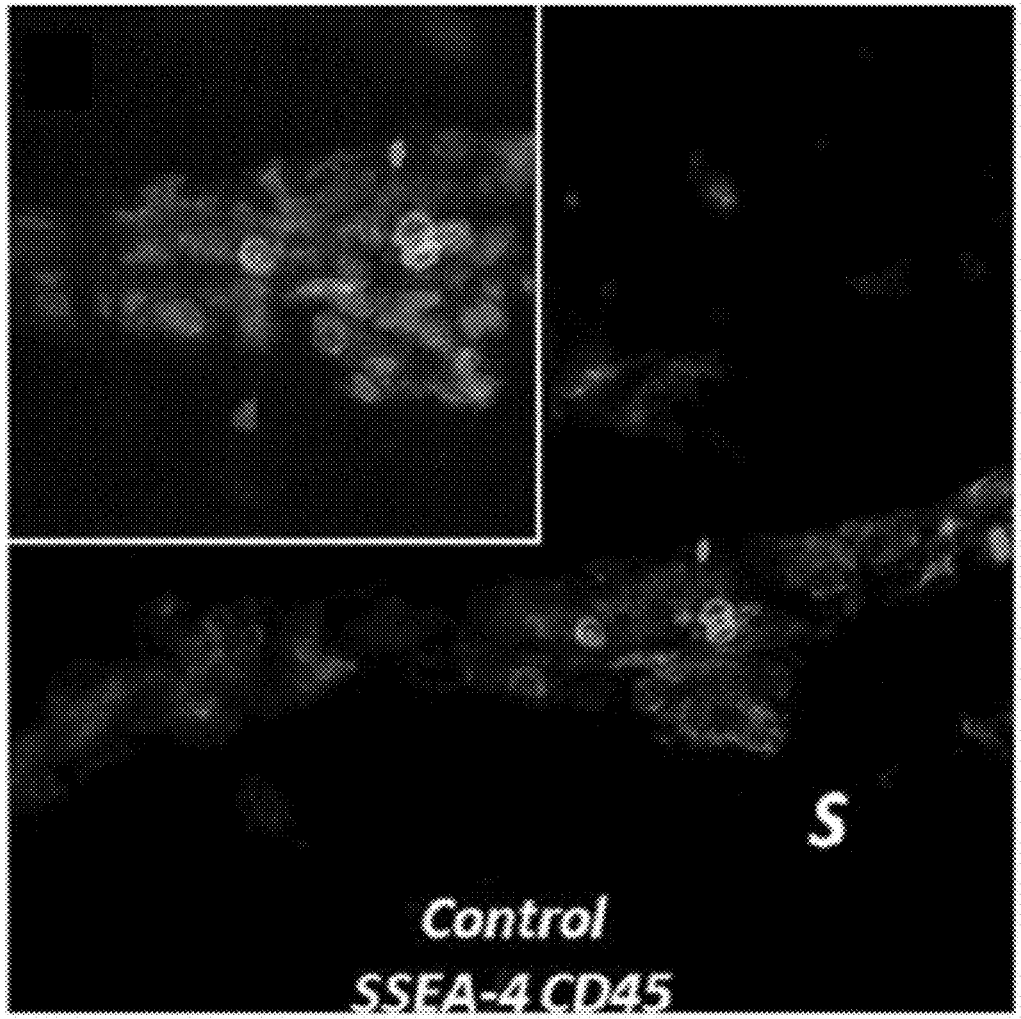
FIG. 6A is an immunohistological stain showing mesenchymal stem cells (MSC) present 7 days after subcutaneously implanting untreated PLGA scaffolds.
Figure 6B:
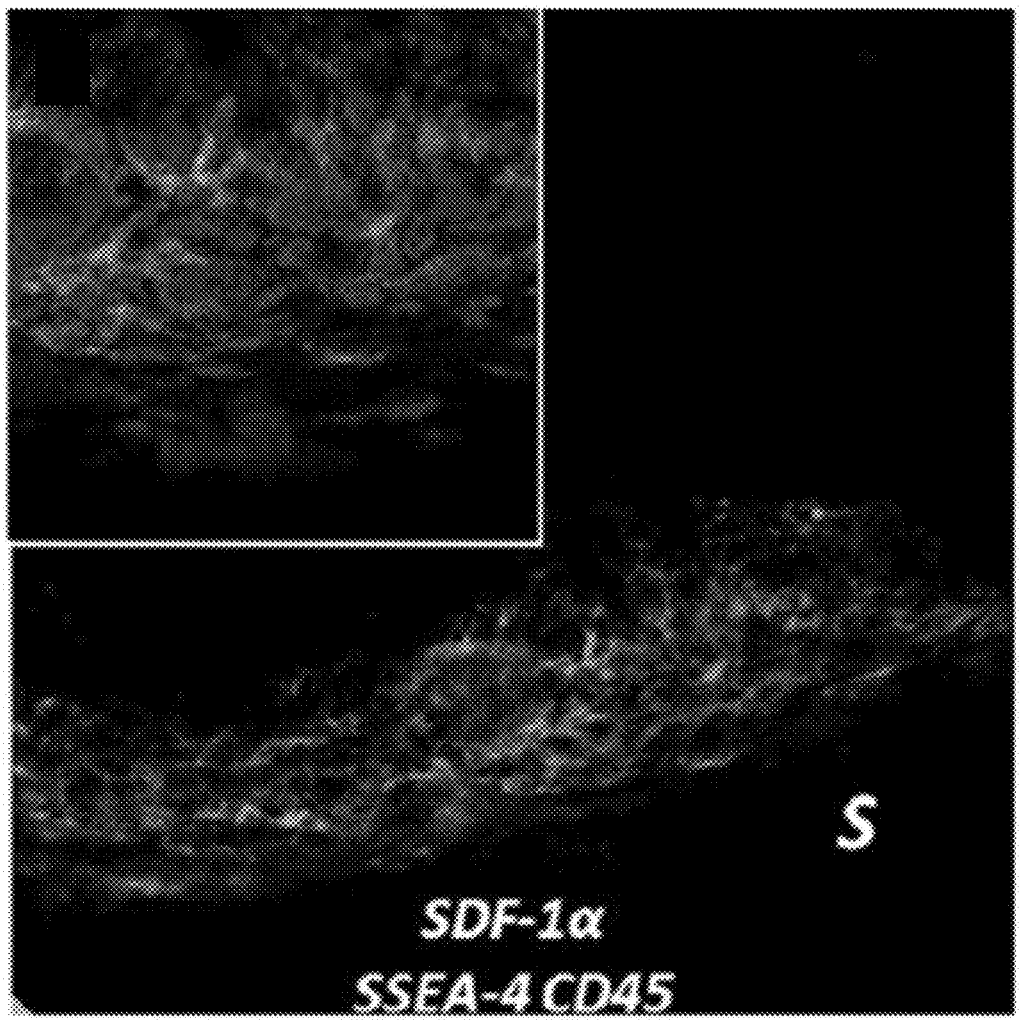
FIG. 6B is an immunohistological stain showing mesenchymal stem cells present 7 days after subcutaneously implanting SDF-1α treated PLGA scaffolds.
Figure 6C:
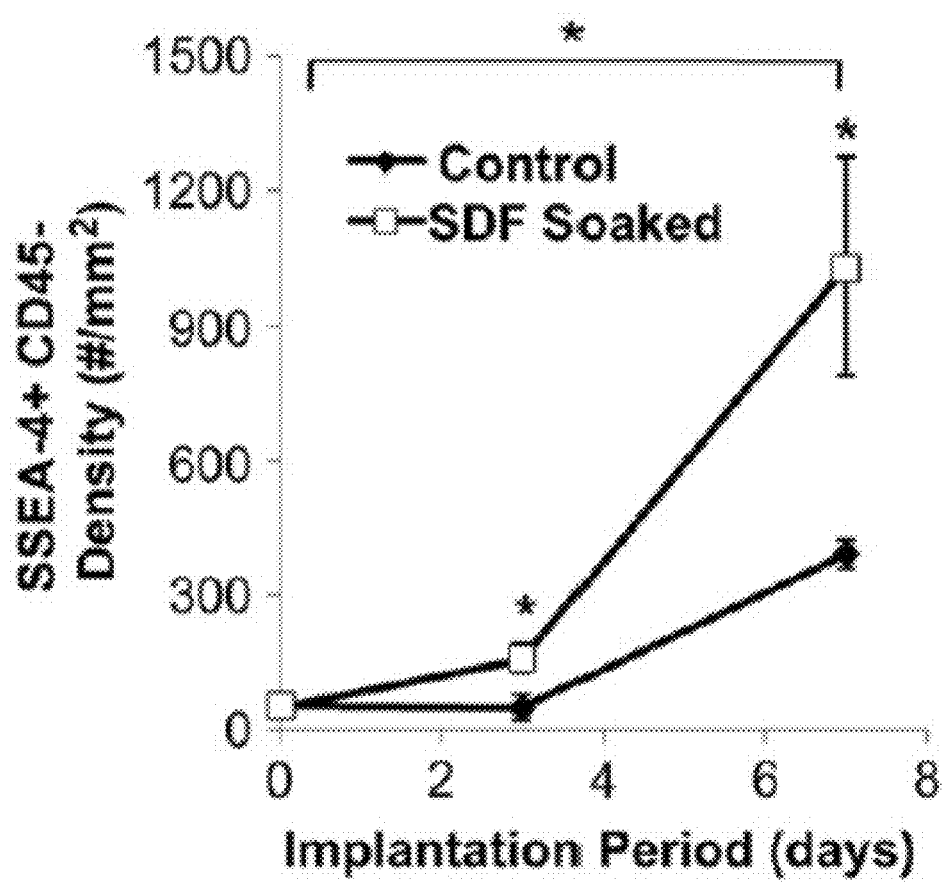
FIG. 6C is a graphical display showing densities of engrafted MSC at Days 3 and 7 for FIGS. 6A and 6B.
Figure 6D:
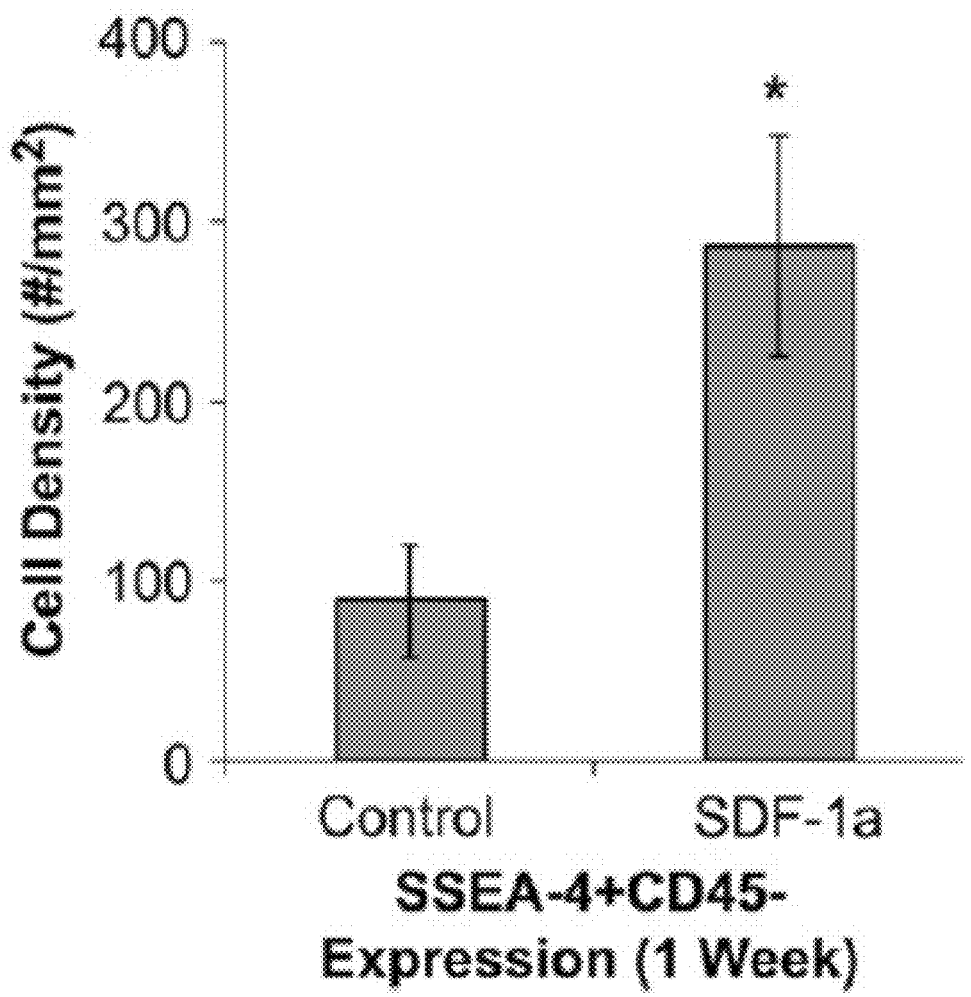
FIG. 6D is a graphical display showing densities of MSC in scaffold interiors for FIGS. 6A and 6B.

To prepare the tissue adhesive, SDF-1α was loaded onto the PLGA scaffolds prepared in EXAMPLE 2, and then implanted into the mouse subcutaneous model. The scaffolds were soaked in SDF-1α solution, and then implanted into a mouse subcutaneous site. Untreated PLGA scaffold was a control. After 7 days implantation, mesenchymal stem cells (MSCs) number in SDF-1α treated scaffolds was significantly higher than in the untreated scaffolds, which evidenced by immunohistological staining shown in FIGS. 6A and 6B, with qualification of the MSCs shown in FIGS. 6C and 6D. Specifically, SDF-1α increases engraftment of MSC (SSEA-4+/CD45− cells) to subcutaneously implanted PLGA scaffolds (SSEA-4, CD45). At Day 7, untreated PLGA scaffolds have very low engraftment of MSCs (FIG. 6A), while SDF-1α treated scaffolds have enhanced MSC engraftment (FIG. 6B). "S" indicates location of the scaffold implants. The density of engrafted MSC was quantified at Days 3 & 7 and compared between treatment groups (FIG. 6C). At both time points, a significant, roughly 3-fold increase in engrafted MSC in the SDF-1α scaffold group was observed, Bonferroni test (P<0.05). The density of MSC in the scaffold interior was also quantified between groups (FIG. 6D), and reveals again a roughly 3-fold increase in MSC density, Student t-test (P<0.05).

Figure 6E:
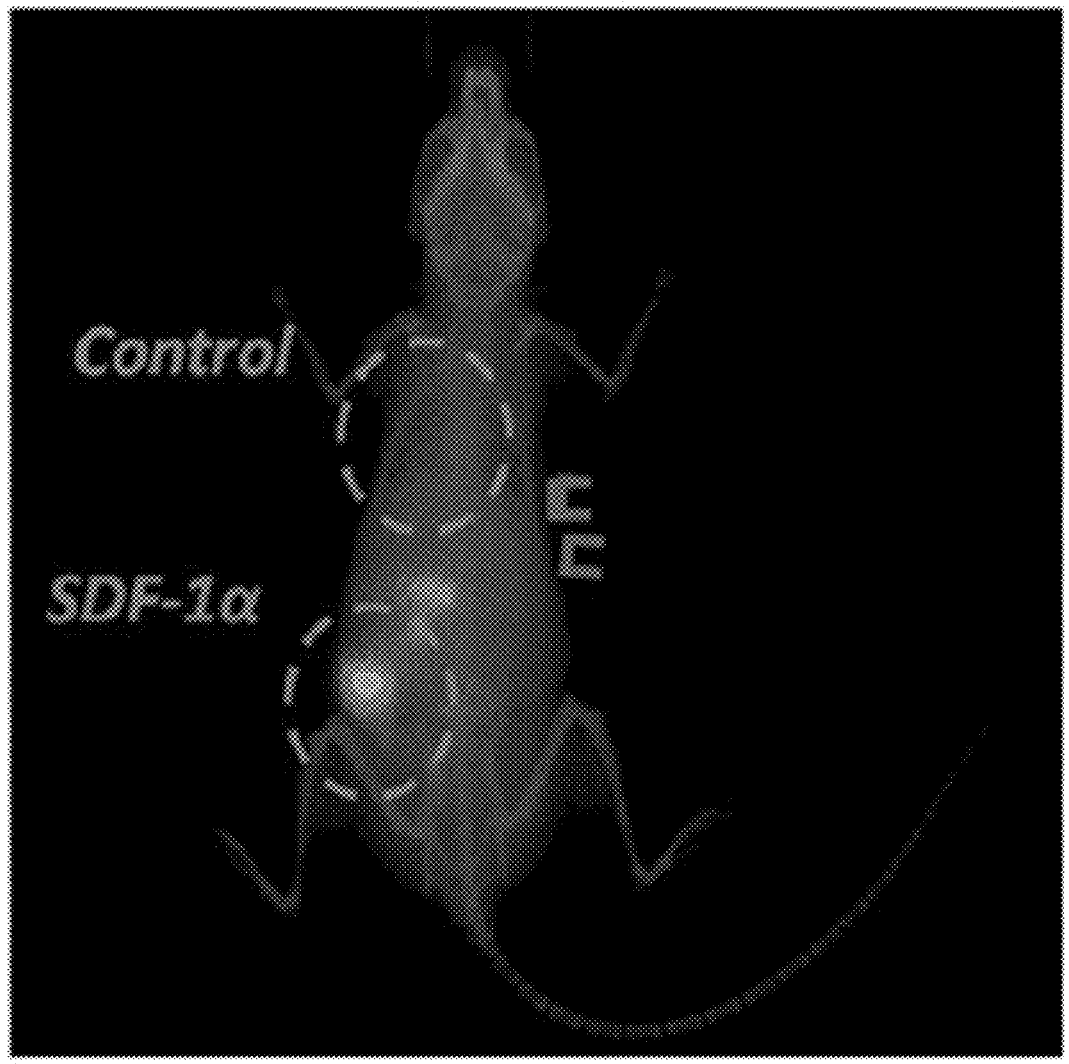
FIG. 6E is a whole body image of a mouse with SDF-1α induced engraftment of a tail vein injected MSC to the site of scaffold implantation 48 hrs after injection.

Furthermore, when injecting MSCs into the mouse with implanted scaffolds from mouse tail vein, the MSCs accumulated in the SDF-1α soaked scaffolds more than in the untreated scaffold through an animal whole body imaging system, as shown in FIG. 6E. This result evidenced SDF-1α release significantly increases engraftment of stem cells into the scaffold, which released SDF-1α in a short-term. A combination of long-term SDF-1α release and bioadhesive can therefore increase stem cell recruitment to enhance and retain long-term tissue bonding.

Figure 7A:
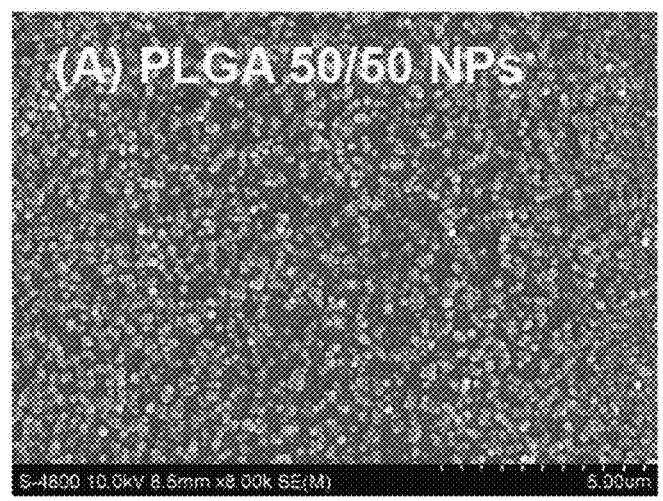
FIG. 7A is a TEM image of SDF-1α loaded PLGA 50/50 nanoparticles with size of 200 nm.

To further examine the feasibility, SDF-1α was loaded into PLGA (lactide/glycolide (LA/GA) ratios: 50/50, 75/25 and 85/15) nanoparticles using double-emulsion methods, and the loaded nanoparticles were tested for release kinetic and cell compatibility. For SDF-1α release, NPs loaded with therapeutic reagent are placed in dialysis tubing (100 kDa M.W. cutoff) and immersed in PBS at pH=7.4 and 37° C. The lysate was collected at different times (up to 1 month) to measure the released compound amount. The release kinetics are tuned by altering PLGA LA/GA polymer molar ratios (50/50, 75/25, and 85/15). The carboxyl groups of PLGA NP surface were activated using carbodiimide chemistry, and then grafted with NHS. FIG. 7A shows a TEM image of SDF-1α loaded onto PLGA 50/50 NPs where the NP size was observed to be ~200 nm. Loading efficiency was observed to be ~50% for all 3 types of NPs.

Figure 7B:
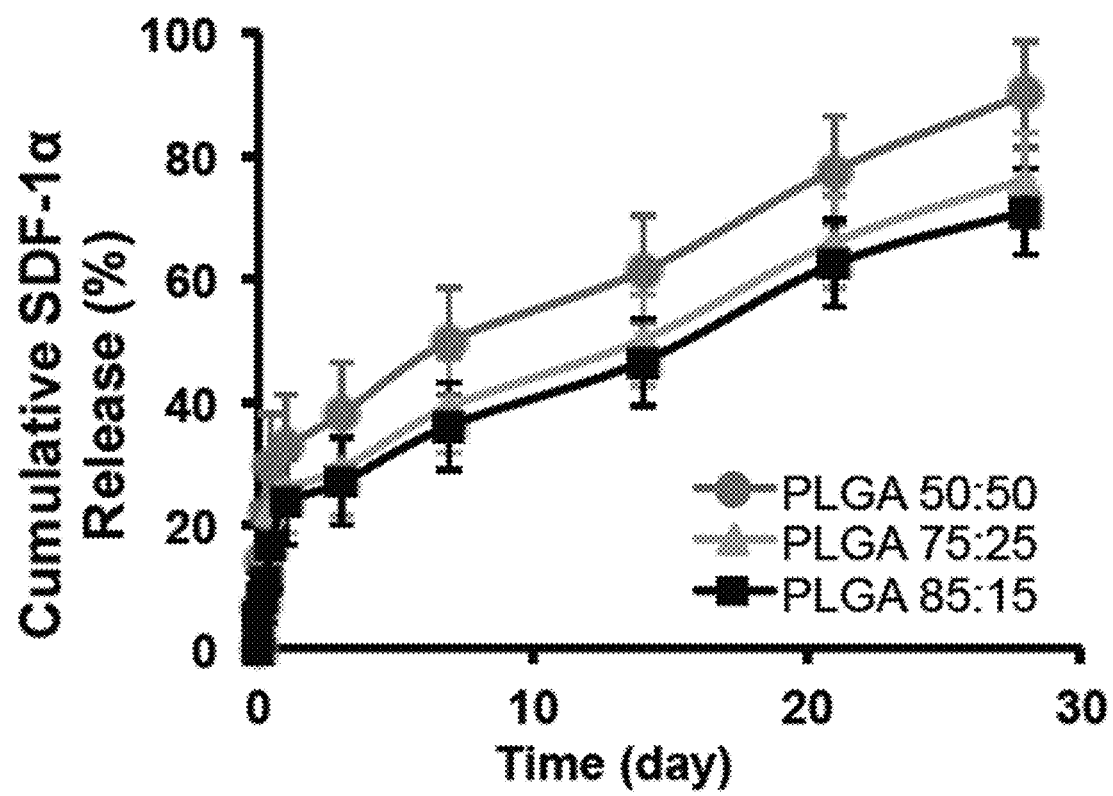
FIG. 7B is a graphical display of SDF-1α release curves from 3 different PLGA nanoparticles in PBS at 37° C. over 4 weeks.
Figure 7C:
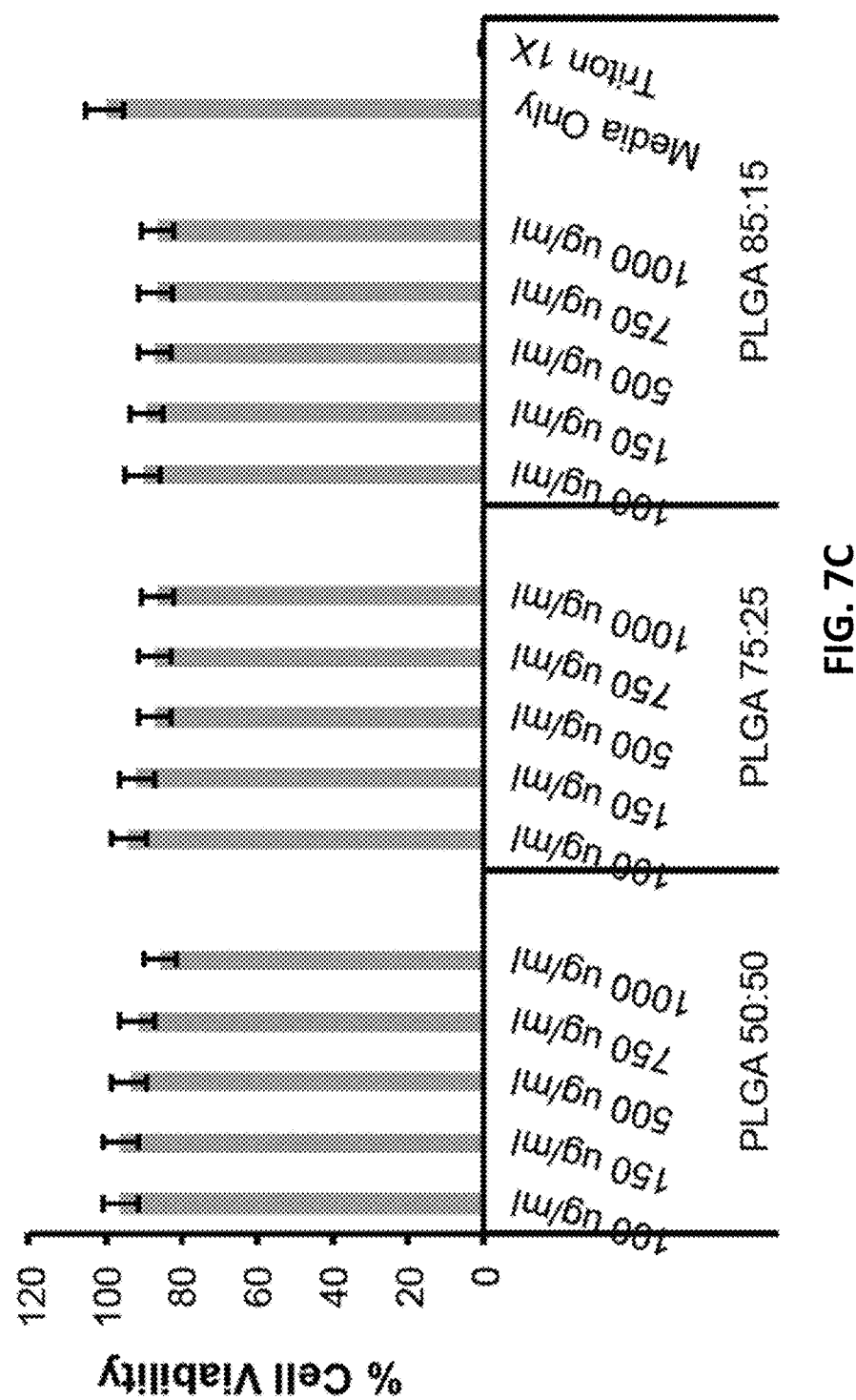
FIG. 7C is a graphical display of Mesenchymal stem cell (MSC) viability for PLGA nanoparticles at different concentrations.

All nanoparticles were observed to release the SDF-1α for more than 4 weeks. After 4 weeks in PBS at 37° C., the SDF-1α was released up to 90% for PLGA 50/50 NPs and up to 70% for PLGA 85/15 NPs, as shown in FIG. 7B. All NPs had burst release (~30%) at day 1 due to protein adsorption, which may be reduced when blended with the hydrogel. Tuning PLGA's lactide/glycolide ratio from 50/50 to 85/15 can alter the SDF-1α release kinetics from the NPs and the blend, and using high LA/GA ratio can extend the protein release kinetics. Also, all NPs at various concentrations (up to 1000 m/mL) showed good cell compatibility when cultured with adipose derived MSCs, as shown in FIG. 7C. Media was used as a positive control and Triton 1× was a negative control. These results indicate that the nanoparticle/hydrogel blend is promise to be delivered into the detachment site and release SDF-1α for a long-term stem cell recruitment in vivo.

Example 5

SDF-1α Stem Cell Recruitment From Tissue Adhesive Compositions

Figure 8:
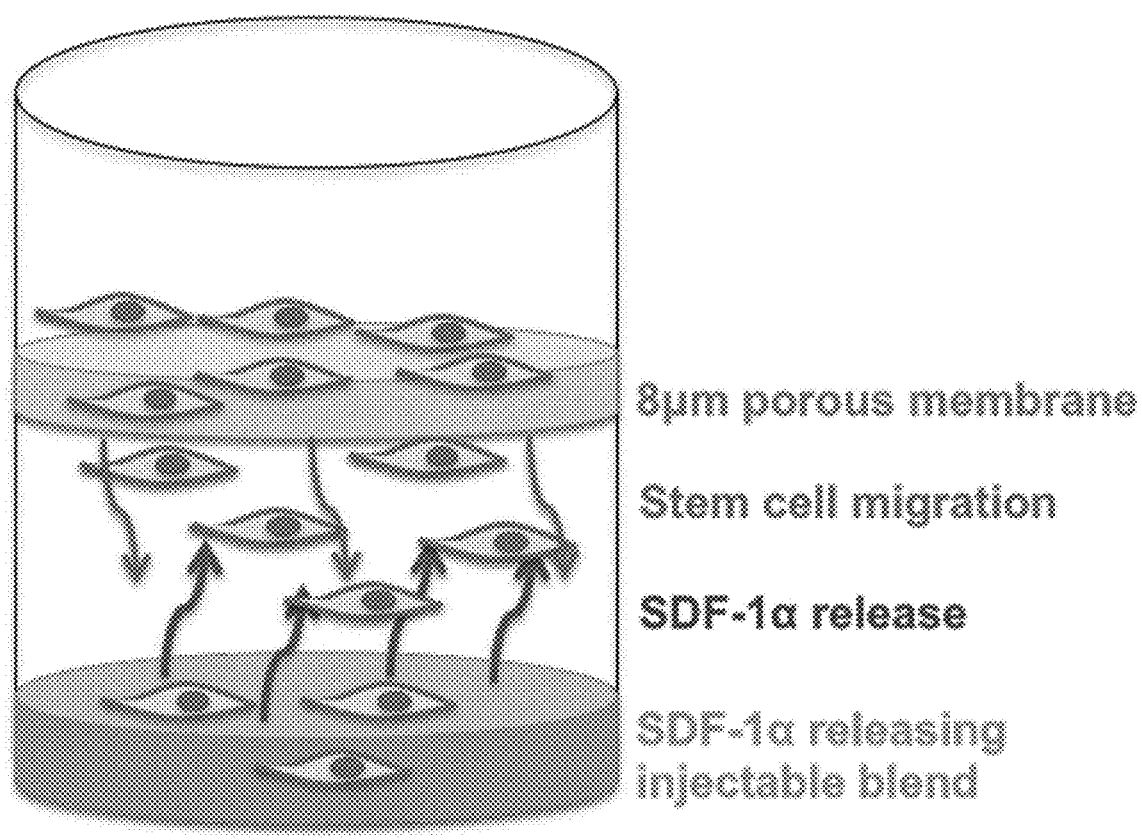
FIG. 8 is a schematic view of a transwell system for evaluating MSC migration for SDF-1α release from a SDF-1α loaded tissue adhesive.

To examine the site directed homing capability of SDF-1α-containing tissue adhesive prepared in EXAMPLE 4, an in vivo homing and engraftment transwell model can be used, as illustrated in FIG. 8. The SDF-1α-containing tissue adhesive can be injected and form a hydrogel in a well of cell culture plates beside transwell inserts in the lower chamber of 8 μm pore membranes of 24-well plates. Prior to the SDF-1α-containing tissue adhesive placement, rat MSCs can be labeled with a cell tracer dye of carboxyfluorescein diacetate succinimidyl ester (CFDA-SE, Invitrogen) and seeded onto the transwell inserts. MSC expansion media is removed and replaced with fresh media in the upper and lower chambers. SDF-1α is allowed to release from the blends into the lower chamber, and the percentage of trans-migrated cells from top chamber to bottom chamber is quantified.

Briefly, membranes will be detached from insert to remove non-migrated cells, and H&E stained to visualize and quantify cell migration to the lower side of the membrane. To verify cell engraftment, the SDF-1α-containing tissue adhesive is be removed from the bottom wells, fixed in cold methanol, and visualized via CFDA-SE staining using known methods. The samples include the SDF-1α-containing tissue adhesive having different SDF-1α dosages, SDF-1α loaded hydrogel, hydrogel alone, nanoparticles alone, and TCPS without SDF-1α. To ensure SDF-1α function after late released from the nanoblend, the cell migration for the samples after 1, 2, 3 and 4 week release in cell culture medium is assessed using the same method as described above.

The optimal SDF-1α releasing bioadhesive found from in vitro stem cell migration, blank bioadhesive, and tissue glue will be utilized for in vivo testing. The whole procedure is the same as discussed in EXAMPLE 4. Besides extracellular matrix staining, mechanical testing, inflammation, SMCs and angiogenesis (the same protocol as in EXAMPLE 4), stem cell recruitment in the implants are investigated. Immunohistological staining for MSCs (CD90+/CD45−), EPCs (CD34, CD133) and HSCs (CD34, Sca-1) are executed to check stem cell type and amount in the explants. Ten animals per group per time points is used. SDF-1α is expected to sustainably release from the SDF-1α-containing tissue adhesive for a month and retain bioactivity. The multiple stem cells are also expected to be recruited to the implant site, and promote the angiogenesis and new smooth muscle tissue formation. It is expected that this method can further enhance vaginal wall attachment, thus preventing further POP development.

The invention claimed is:

1. A tissue adhesive composition comprising:
  a biodegradable adhesive;
  nanoparticles; and
  a tissue regenerative agent,
 wherein the nanoparticles are loaded with the tissue regenerative agent, and
 wherein the composition has a lap shear strength greater than 35 kPa when adhered to a biological tissue to tissue interface for 1 hour,
  wherein the biodegradable adhesive comprises a dopamine grafted alginate, polytripeptide (Gly-Tyr-Lys), Mussel Adhesive Protein (MAP), polyethylene glycol (PEG-DOPA), hyaluronic acid (HA) on Pluronic hydrogel, catechol-Ala-Ala-PEG (CAAPEG), poly ((Lys·HBr)$_x$-(DOPA)$_y$), deacetylated chitosan, oxidized and DOPA-functionalized dextran, PEG-dopamine-polycaprolactone (PCL), injectable citrate-based mussel-inspired bioadhesives iCMBAs, anti-bacterial and anti-fungal iCMBAs (AbAf iCs), click iCs, ethylene glycol acrylate methacrylate dopamine (EGAMA-DOPA), poly (dopamine-co-acrylate) (PDA), rfp-1 (MAP), light-activated, mussel protein-based bioadhesive (LAMBA), PEU (poly (CATyr-co-Leu)), PEU (poly (CA-Ser-co-Leu-co-PPG)), POEC-d (octanediol, PEO, citric acid, dopamine), DCTA (gelatin macromer, $Fe^{3+}$, genipin), a polyester, 4-arm-PEG-DA, 4-arm-PEG-PBA, polypeptide-pluronic-polypeptide, or any combination thereof;
  wherein the biodegradable adhesive is present in a concentration of 1 to 40 wt. % and comprises a polymer having a weight average molecular weight of 20,000-200,000;
  wherein the nanoparticles comprise poly (lactic acid) (PLA), poly (glycolic acid) (PGA), poly (lactide-co-glycolide) ("PLGA"), poly (lactide-co-glycolide) N-hydroxysuccinimide ("PLGA-NHS"), poly (lactide-co-glycolide) polydopamine ("PLGA-Dopa"), polydopamine, hyaluronic acid-dopamine, silica, poly-(ethylene glycol) (PEG), poly (acryl amide) (PAA), poly (vinyl pyrrolidone) (PVP), poly (caprolactone) (PCL), chitosan, poly-alkyl-cyano-acrylates (PAC), gelatin or any combination thereof;
  wherein the nanoparticles have an average particle size in any dimension of 50 nm to 500 nm;
  wherein the tissue regenerative agent comprises a cell recruitment agent, a tissue growth factor, a protein, a microRNA, an exosome, or any combination thereof;
  wherein the tissue regenerative agent comprises a cell recruitment agent; and
  wherein the cell recruitment agent is stromal cell derived factor-1 alpha ("SDF-1α").

2. The composition of claim 1, wherein the biodegradable adhesive comprises a functionalized biopolymer.

3. The composition of claim 1, wherein the biodegradable adhesive is a dopamine-grafted biopolymer.

4. The composition of claim 3, wherein the biodegradable adhesive comprises a dopamine-grafted alginate.

5. The composition of claim 4, wherein the dopamine-grafted alginate is crosslinked to form a hydrogel.

6. The composition of claim 1, wherein the nanoparticles are biodegradable.

7. The composition of claim 6, wherein the nanoparticles comprise PLGA and/or PLGA-NHS having a weight average molecular weight of 50,000-120,000.

8. The composition of claim 1, wherein the nanoparticles have an average particle size in any dimension of 250 nm or less.

9. The composition of claim 1, wherein the nanoparticles are present in a concentration of up to 15 wt. %.

10. The composition of claim 1, wherein the composition has a lap shear strength of a least 20 kPA when adhered to a biological tissue to tissue interface.

11. The composition of claim 1, wherein the cell recruitment agent recruits mesenchymal stromal/stem cells ("MSCs"), hematopoietic stem cell ("HSC"), and/or endothelial progenitor cell ("EPC").

12. The composition of claim 1, wherein the cell recruitment agent increases regenerative cell populations within a biological environment where the composition is present.

13. The composition of claim 1, wherein the tissue regenerative agent is released from the composition into the biological environment over 1-50 days.

14. The composition of claim 12, wherein the biological environment is mammalian tissue.

15. The composition of claim 1, wherein the tissue regenerative agent is encapsulated in the nanoparticles.

16. A method of adhering tissue comprising:
applying a film of a composition according to claim 1 to a first surface of a first biological tissue;
contacting a second surface of a second biological tissue with the first surface of the first biological tissue, wherein the film of the composition is positioned between and in contact with both the first surface and the second surface.

17. A tissue adhesive composition comprising:
a biodegradable adhesive;
nanoparticles; and
a tissue regenerative agent,
wherein the nanoparticles are loaded with the tissue regenerative agent, and wherein the composition has a lap shear strength greater than 35 kPa when adhered to a biological tissue to tissue interface for 1 hour,
wherein the biodegradable adhesive is present in a concentration of 1 to 40 wt. % and comprises a polymer having a weight average molecular weight of 20,000-200,000;
wherein the biodegradable adhesive comprises a dopamine grafted alginate;
wherein the nanoparticles have an average particle size in any dimension of 50 nm to 500 nm;
wherein the nanoparticles comprise poly (lactide-co-glycolide) ("PLGA"); and
wherein the tissue regenerative agent comprises stromal cell derived factor-1 alpha ("SDF-1α").

* * * * *